United States Patent
Wach et al.

(10) Patent No.: US 6,404,953 B1
(45) Date of Patent: Jun. 11, 2002

(54) OPTICAL ASSEMBLY WITH HIGH PERFORMANCE FILTER

(75) Inventors: Michael L. Wach, Atlanta, GA (US); Dwight Holter, Naples, FL (US); Eric T. Marple, Atlanta, GA (US)

(73) Assignee: Cirrex Corp., Altanta, GA (US)

( * ) Notice: Subject to any disclaimer, the term of this patent is extended or adjusted under 35 U.S.C. 154(b) by 0 days.

(21) Appl. No.: 09/318,451

(22) Filed: May 25, 1999

Related U.S. Application Data

(63) Continuation-in-part of application No. 08/819,979, filed on Mar. 13, 1997, now Pat. No. 5,953,472.
(60) Provisional application No. 60/013,341, filed on Mar. 13, 1996, provisional application No. 60/036,504, filed on Jan. 28, 1997, and provisional application No. 60/038,395, filed on Feb. 14, 1997.

(51) Int. Cl.[7] .................................................. G02B 6/26
(52) U.S. Cl. ............................. 385/31; 385/24; 359/577
(58) Field of Search ..................... 385/31, 12, 115–123, 385/37, 49, 24, 29; 359/566, 577, 586

(56) References Cited

U.S. PATENT DOCUMENTS

| | | | |
|---|---|---|---|
| 3,796,905 A | 3/1974 | Tomii et al. | 313/92 |
| 3,874,783 A | 4/1975 | Cole | 350/96 |
| 3,906,241 A | 9/1975 | Thompson | 250/574 |
| 3,910,677 A | 10/1975 | Becker et al. | 350/96 |
| 4,191,446 A | 3/1980 | Arditty et al. | 350/96 |
| 4,380,365 A | 4/1983 | Gross | 350/96.13 |
| 4,449,535 A | 5/1984 | Renault | 128/634 |
| 4,573,761 A | 3/1986 | McLachlan et al. | 350/96.24 |
| 4,615,581 A | 10/1986 | Morimoto | 350/96.21 |
| 4,654,532 A | 3/1987 | Hirschfeld | 250/458.1 |
| 4,707,134 A | 11/1987 | McLachlan et al. | 356/342 |
| 5,878,178 A | 3/1999 | Wach | 385/55 |
| 5,901,261 A | 5/1999 | Wach | 385/38 |
| 5,911,017 A | 6/1999 | Wach et al. | 385/12 |
| 6,269,202 B1 * | 7/2001 | Lee et al. | 385/241 |

FOREIGN PATENT DOCUMENTS

| | | |
|---|---|---|
| EP | 0185782 | 7/1986 |
| EP | 0210869 | 2/1987 |
| EP | 0286419 | 10/1988 |
| WO | WO 97/34175 | 9/1997 |
| WO | WO 97/48995 | 12/1997 |

OTHER PUBLICATIONS

Boiarski A., "Fiber Optic Particle Concentration Sensor", *SPIE vol. 566 Fiber Optic and Laser Sensors III*, 1985, pp. 122–125.

Krohn D., "Intensity Modulated Fiber Optic Sensors Overview", *SPIE vol. 718 Fiber Optic and Laser Sensors IV*, 1986, pp. 2–11.

McCann, B., "Specialty Optical Fibers Resolve Challenging Application Problems", *Lightwave*, Nov. 1994, pp. 48, 51–52.

Tan, W. et al., "Submicrometer Intracellular Chemical Optical Fiber Sensors", *Science*, vol. 258. Oct. 30, 1992, pp. 778–781.

* cited by examiner

*Primary Examiner*—Phan T. H. Palmer
(74) *Attorney, Agent, or Firm*—King & Spalding

(57) ABSTRACT

Optical assembly for controlling or limiting undesirable photon entrance, reflection, departure, or appearance. A material opaque to unwanted photons can be applied to an optical assembly that would otherwise allow penetration of the unwanted photons. For example, a filter can be applied to a waveguide member. A first face surface of the filter faces toward an end of the waveguide member and a second face surface of the filter faces away from that member end. A mask adheres to one of the filter surfaces. The mask is substantially opaque in at least some selected spectral region to impact the extent to which photons in that spectral region can pass through the filter and to the waveguide member.

51 Claims, 4 Drawing Sheets

OPTICAL ASSEMBLY WITH HIGH PERFORMANCE FILTER

STATEMENT REGARDING RELATED APPLICATIONS

This application is a continuation in part of U.S. patent application Ser. No. 08/819,979, filed Mar. 13, 1997, entitled "Method and Apparatus for Improved Fiber Optic Light Management," now issued as U.S. Pat. No. 5,953,477, and is related to U.S. patent application Ser. Nos. 08/561,484 now U.S. Pat. No. 5,764,840, entitled "Optical Fiber with Enhanced Light Collection and Illumination and Having Highly Controlled Emission and Acceptance Patterns," filed Nov. 20, 1995, now issued as U.S. Pat. No. 5,764,810, 09/267,258, entitled "Method and Apparatus for Filtering an Optical Fiber" filed Mar. 12, 1999, and Ser. No. 09/280,413 U.S. Pat. No. 6,208,783, entitled "Optical Filtering Device," filed Mar. 29, 1999, and U.S. Provisional Application Serial Nos. 60/013,341, entitled "Fiber Optic Interface with Manipulated Delivery and Reception Sensitivities," filed Mar. 13, 1996, Ser. No. 60/036,504, entitled "Improved Fiber Optic Probe Assembly," filed Jan. 28, 1997, and Ser. No. 60/038,395, entitled "Improved Filtering of Optical Fibers and Other Related Devices," filed Feb. 14, 1997.

TECHNICAL FIELD

This invention relates generally to optical assemblies, and more particularly to assemblies including waveguides, for example optical fibers, in optical connection with high performance filters.

BACKGROUND OF THE INVENTION

Optical assemblies including waveguides in recent years have been recognized as offering a high potential for solving problems in a number of commercial applications including telecommunications and medical diagnostics. Optical fiber assemblies are well known in telecommunications and have been found to be especially useful in analyzing materials by employing various types of light-scattering spectroscopy. Optical filters have been found to be useful in such applications. In telecommunications typical uses include bandpass filters in wavelength-division multiplexing and as noise blocking filters for optical amplifiers.

The term "waveguide" is used herein to refer to an optical structure having the ability to transmit light in a bound propagation mode along a path parallel to its axis, and to contain the energy within or adjacent to its surface. In many optical applications it is desirable to filter light that is propagating within a waveguide, perhaps an optical fiber, in order to eliminate or redirect light of certain wavelengths or to pass only light of certain wavelengths.

Many types of filters, including interference filters, are commonly used for this filtering. However, there are a number of difficulties associated with the use of many types of filters, including interference filters. First, in some applications the power density of light propagating within a waveguide may be unacceptably high for the filter, having detrimental effects that may include damage to the filter material or reduced filter performance.

Also, filters are typically employed by means of bulky, multiple-optical-element assemblies inserted between waveguides, which produces a variety of detrimental effects. Separate optical elements can be difficult to align in an assembly and it can be difficult to maintain the alignment in operation as well. Each element often must be separately mounted with great precision and the alignment maintained. Also, an increase in the number of pieces in an optical assembly tends to reduce the robustness of the assembly; the components may be jarred out of alignment or may break. In addition, interfaces between optical elements often result in significant signal losses and performance deterioration, especially when an air gap is present in the interfaces. The materials of which the additional elements are composed may also introduce fluorescence or other undesirable optical interference into the assembly.

The size of filtering assemblies is often a problem as well. Not only can it be difficult to manufacture a filter on a small surface area, but also filtering assemblies usually contain bulky light-collimating, alignment and mounting components in addition to the filtering element. However, space is often at a premium in optical assemblies. In addition, the filtering characteristics of interference filters change depending upon the angle at which light is incident on the filter, and interference filters are generally designed for the filtration of normally incident light.

High performance filters have shown particular promise in many applications as described in Applicants' co-pending U.S. patent application Ser. No. 09/267,258 and U.S. Pat. No. 5,953,477. There is an ongoing demand for assemblies in these and other industrial and medical applications that have less noise. In telecommunications the demand for more useable bandwidth is growing at an incredible rate. That telecommunications demand and the recognized need for more effective medical and environmental diagnostic tools (for example those described in the referenced U.S. patent application Ser. No. 08/819,979 now issued as U.S. Pat. No. 5,953,477) are resulting in the need for assemblies having improved signal to noise ratio.

SUMMARY OF THE INVENTION

This invention provides a surprisingly effective optical noise reduction in optical assemblies by controlling or limiting unwanted photon entrance, reflection, departure or appearance in or from the assembly. Applicants have found such unwanted photons passing through areas that had not been recognized or had been vastly underestimated as photon passageways potentially creating significant problems. Applicants have further found the optical performance loss because of these areas to present special, technology limiting problems in applications benefiting from high performance filters. More specifically, applicants have found that penetration of unwanted photons especially in areas along periphery of the filter layers, even very thin filter layers, can cause significant noise or effective signal erosion. This is especially true when optical transmission purity/high optical performance is essential. That unwanted photon penetration occurs not only through edge surfaces but also through face surfaces and edge junctures. The edge juncture is where the filter edge surface joins a filter face surface or a filter face surface joins another face, for example, of a waveguide, including an optical fiber. Problematic optical noise can occur through the filter face itself if, for example, some areas of the filter or the waveguide to which it is optically connected have differing transmission characteristics or demands. In accordance with this invention improvements are obtained by selectively covering with a material opaque to the unwanted photons those areas that would otherwise allow the unwanted penetrations. Assemblies according to one embodiment of the invention when used to cover such junctures can effectively be utilized as universal adapters for connecting fibers to one another or to optical devices for specific applications, for example, in chemical analysis and or communication facilitating devices. A fiber identification mechanism assures proper fiber matching and alignment.

DETAILED DESCRIPTION

Figure 1:
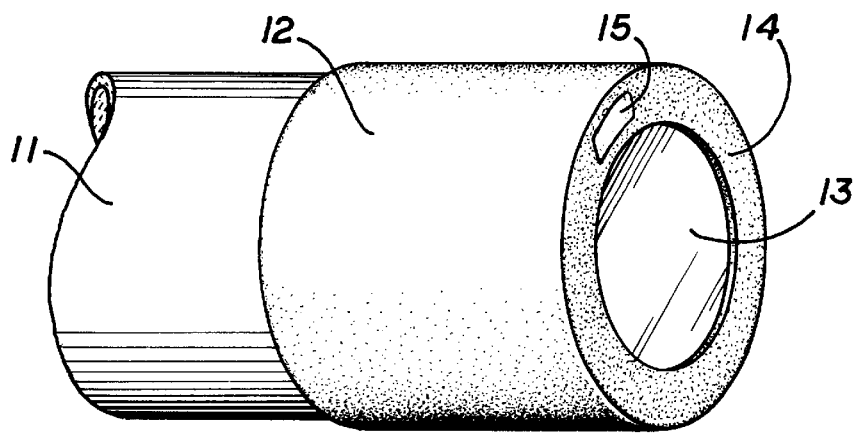
FIG. 1 is a perspective of an optical assembly end portion illustrating a masked, filtered fiber end.
Figure 2:
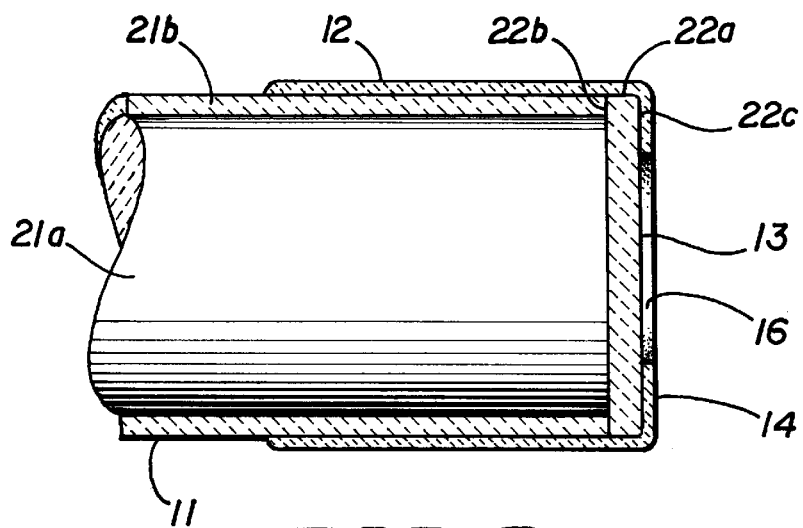
FIG. 2 is a cross sectional magnified view of an optical assembly in accordance with FIG. 1 with exaggerated fiber core, filter, and mask thickness dimensions.

A preferred embodiment of the present invention is illustrated in FIG. 1 and FIG. 2. In FIG. 1 the end of an elongated waveguide, in the illustration an optical fiber 11, is shown having at its end mask 12. Mask 12 partially covers the filter end face 13 at the end face periphery 14. Mask 12 is opaque to at least some wavelengths of light. Accordingly, light of the opacity wavelengths do not penetrate mask 12 thereby eliminating unwanted optical noise that would result from such light penetration of the mask covered areas. Such optical noise is particularly problematic in applications requiring high performance, for example, in high bandwidth telecommunications, and those applications requiring the ability to differentiate between ordinarily small signal differences, such as in Raman spectroscopy. Applicants' co-pending U.S. patent application Ser. No. 09/267,258 now U.S. Pat. No. 6,174,424 describes high performance filters that are an important factor in enabling the user to get to new performance levels. For the foreseeable future there is a conspicuous need for ever increasingly higher performance levels. Applicants have found the apparently extreme measures according to this invention to enable performance levels at which the otherwise tolerable noise is problematic. In accordance with a preferred embodiment of the present invention high performance filters combined with masking eliminates significant sources of unwanted light penetration.

U.S. patent application Ser. No. 08/819,979, now issued as U.S. Pat. No. 5,953,477 referenced above describes filter performance requirements for demanding applications, such as Raman spectroscopy. These requirements include: a) high throughput in transmission wavelength region; b) high-attenuation (dense) blocking in rejection wavelength regions; c) steep transition between wavelength regions of rejection and transmission; d) environmental stability; e) low ripple in passage regions, f) minimal sensitivity to temperature variation; g) no performance fluctuation with ambient humidity or chemicals; h) the ability to withstand high, and rapidly changing, temperatures present in sterilization processes and industrial processes; i) physical toughness; and j) tenacious adhesion between filter and substrate.

These desirable filter performance properties are achieved in high performance filters, thin-film filters having a large number of alternating high/low refractive indices, stacked layers deposited on a substrate. Between 20 and 150 layers are usually required depending on such factors as: 1) the performance required for the end use; 2) the refractive index differential between materials in adjacent filter layers; 3) the consistency and purity of the filter layer; and 4) the sophistication of the filter design process. And, the layers must be free from defects and voids such that the material characteristics of the layer approaches that of a bulk solid and the packing factor of the layer approaches 100%. Achieving high-density packing requires the molecules depositing onto the substrate to be highly energetic. During the layer deposition process, this energy prevents the forming layer from orienting itself into columnar or similar structures that are riddled with voids. While the depositing layers are predisposed to forming the imperfect structures, the high energy forces pack the molecules (or atoms) into any voids or pinholes which may exist.

Even though the techniques described in U.S. Provisional Application Serial No. 60/038,395 provide an extremely attractive means of filtering optical fibers, the present invention provides further and now recognizable signal quality improvements. The present invention has particular advantages for instrumentation applications, such as Raman, fluorescence, and other spectroscopic analyses. They are also devised for wavelength division multiplexing, telecommunications, general fiber optic sensor usage, photonic computing, photonic amplifiers, pump blocking, fiber-integral active devices such as fiber-coupled (pigtailed) lasers and lasers utilizing the fiber as the lasing cavity.

In one embodiment of the present invention, a thin-film interference filter is applied to a fiber end face. The fiber core may have an essentially uniform cross section. Alternatively, the fiber, monomode or multimode, may be up tapered so that the cross section of the core is enlarged at the filter end face and filtered light is angularly redirected or collimated. The filter has a packing density of at least 95%, but preferably greater than 99%. A fiber with an integral, masked filter is utilized for analytical instrumentation/sensing applications generally and spectroscopy more specifically showing improvement even over applicants' previous advanced probe systems. The coating of the filters on the fibers can be accomplished especially effectively by a method described in applicants U.S. patent application Ser. No. 08/819,979, now issued as U.S. Pat. No. 5,953,477, discussed in more detail below in reference to FIG. 4 and FIG. 5. The utilization of high packing density filters in conjunction with up tapered fibers is described in applicants U.S. patent application Ser. No. 09/280,413 now U.S. Pat. No. 6,208,783.

Figure 8:
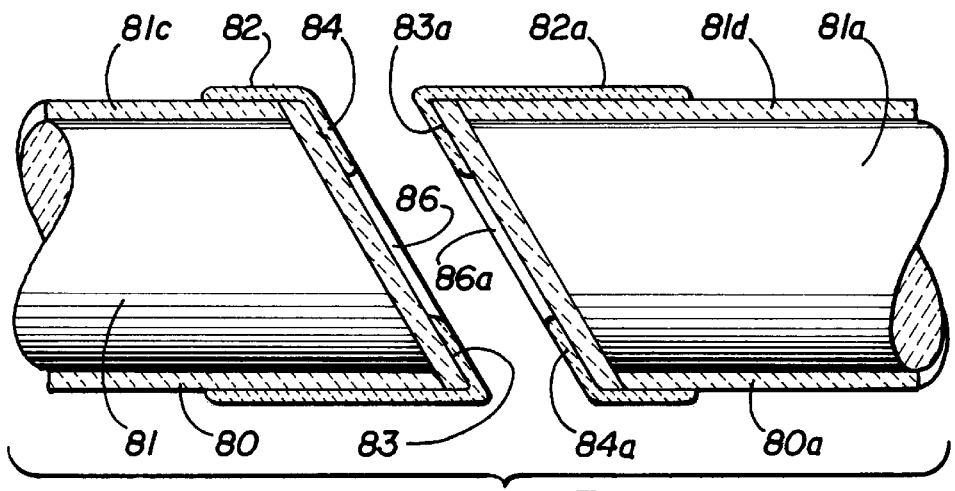
FIG. 8 is a cross sectional view illustrating two optical assemblies each having beveled end faces with mask end near mask end configuration illustrating mating orientation, with exaggerated fiber core, filter, and mask thickness dimensions.

As shown in FIG. 8, described in further detail below, the filter can be applied at an angle of approximately 45 degrees such that the reflected and transmitted light can be transmitted to locations in an optical assembly for subsequent processing. The filter can be oriented at an angle greater than the maximum angle of light propagation within the fiber so that reflected light from the filter cannot back propagate during low-light spectroscopy application, such as Raman. Variability can be introduced into the thin-film application process so that filters of various wavelengths can be produced within a batch. The variability can be provided by masks, intermittent blocking of the deposition particles, off centering, and raising and lowering the substrate. The slightly different filters can be graded and sorted.

Figure 7:
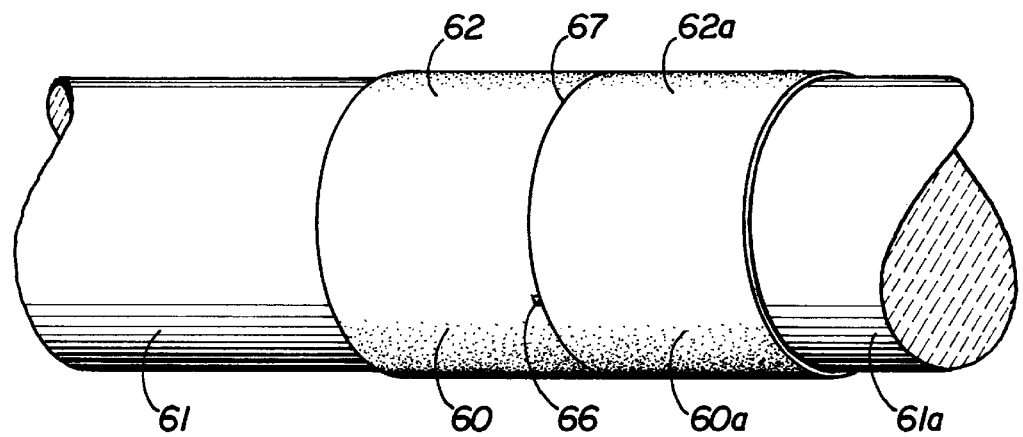
FIG. 7 is a perspective of two optical assemblies in accordance with FIG. 3 in mask end to mask end, mating connection.

Several short, filtered fiber segments can be aligned end-to-end with one another. One end of each fiber segment is angled and has a filter applied to its surface. The opposite, unfiltered ends of the fiber segments may be flat or formed with mating bevels. The filters are slightly offset in wavelength from one another. The assembly can used to tap off signals according to wavelength. or input wavelength-separated signals as illustrated in FIG. 7.

The preferred thin-film deposition processes impart sufficient energy to the depositing molecules so that the forming structure is essentially fully packed (100% comprised of the desired molecules, essentially nonporous, and free of voids and pinholes). For best performance, the structure should approach or equal 100% (greater than 99%) packing density, but at least 95%. Due to this and other factors, adherence to the fiber substrate is tenacious. The effects of the residual mechanical stresses created as a result of the high energy deposition of the filter material are negligible since the fiber is very strong in relation to its diameter. Several thin-film processes are particularly well suited to produce this high-density, hard-coated filter. These processes include magnetron sputtering, single- and dual-beam ion sputtering, ion plating, and ion-assisted deposition (typically slightly less performance and lower packing densities). Reactive -and nonreactive versions of these processes are available. The reactive processes are typically faster in terms of the time required to produce a thin-film coating. These and similar processes contrast with conventional processes, such as evaporative films, which achieve packing densities of approximately 80%. Ion-assisted deposition produces films with densities typically in the 95% range and for this reason are less preferable. In short, a filter with high packing density greater than 99%, preferably approaching or equaling 100%, but at least 95%—is applied directly to the fiber end face utilizing highly energetic, non-conventional thin-film deposition processes.

Fiber optic applications benefit from the availability of filtered fibers with slightly varied wavelengths. These applications include: 1) wavelength division multiplexing (input and output); 2) tapping off spectroscopic wavelengths for detection; and 3) matching filters to lasers with varying but closely grouped wavelengths.

Figure 6:
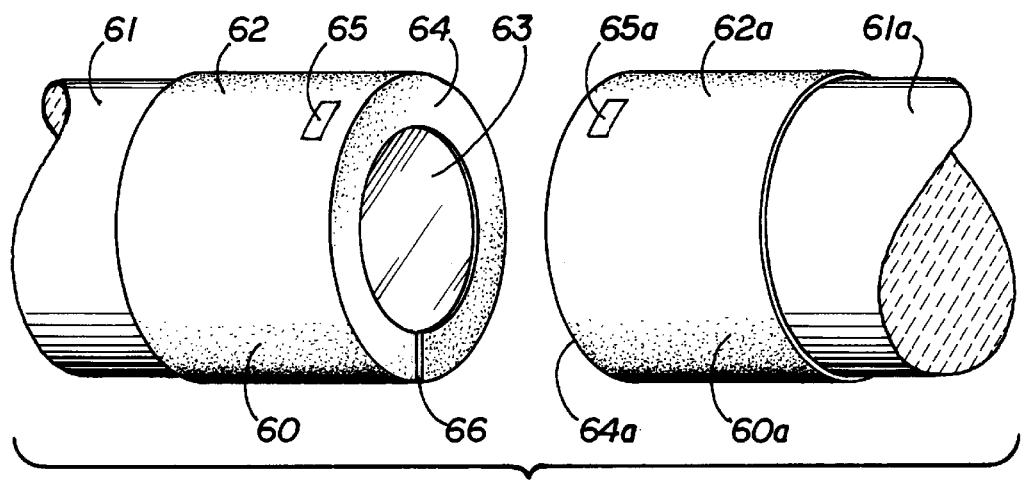
FIG. 6 is a perspective of two optical assemblies with masks placed in mask end near mask end configuration illustrating mating orientation.

In a further preferred embodiment of this invention the mask serves as a significant component in facilitating mating with other waveguide structures. Space 15 is reserved for micro bar code, magnetic or other identification information that will assist in assuring appropriate alignment and mating of the optical assemblies. For example, the mask dimensions and characteristics could be identified. In addition the fiber's core and polarization axes can be identified with respect to the location of the identifier and the mask aperture location, configuration and dimensions. Also, the core dimension and location can be identified. When fiber to fiber connections are made, often testing and aligning can be a time consuming task. Proper information in the identifier space could minimize the testing burden. Using code in identifier space 15 to reference specific, detailed computer link information would allow for unlimited information about the optical assembly. The identifier information could be located at other locations on the mask, but the space is desirably located where it could be used in automating manufacturing systems. If the optical assembly is likely to be end to end connected to another assembly in which subsequent identification is useful, for example as illustrated in FIG. 6 and FIG. 7, an identifier on the edge can be used.

The mask of this invention is an integral part of the operable optical assembly. Thus, it is desirable that the mask be robust and adhere to the filter in a manner that it is not too easily removable. The masking material for the present invention can be applied in a number of ways and can be made of a variety of materials, including metals, oxides and plastics. The precise manner of forming the mask of this invention and the material used in any given application depends on its environmental demands. Fluorinated plastics sold under the trademark Teflon and black epoxy work well in many chemical applications. Durable metallic masks, for example, silver or platinum, are used in a particularly advantageous embodiment of this invention. These metallic masks can be applied using, for example, precision machining or electrolytic deposition and plating techniques. By using photo-resist material and standard photoresist techniques (see, for example, the descriptions for temporary mask formation in U.S. Pat. No. 5,237,630 to Hogg et al.) a temporary mask is formed in surface areas of the pre-assembly filtered fiber that are not to be covered with the durable mask. The temporary mask photoresist material is applied uniformly over the entire filtered fiber end portion. The photoresist material is then exposed imagewise (to distinguish where the durable mask is and is not to be). The photoresist is removed (usually by solvent wash) from the areas where the durable mask is to be. The metallic layer is then deposited, e.g. by electrolytic deposition, over the entire filtered fiber end portion. As the temporary mask is removed using a solvent wash (with a different solvent) any metallic deposition covering the temporary mask is also removed leaving only the durable metallic mask.

Because the durable mask must withstand rigors of an operational environment and adhere firmly to the substrate filter and/or fiber it is important in many deposition environments to assure that the substrate be thoroughly clean before applying the durable mask material. A particularly advantageous method for applying the durable mask uses photoresists in another conventional manner, different from that described above. The fiber end portion is first cleaned thoroughly and then coated over its entire surface with the durable mask material to the desired thickness. Then a photoresist is applied over the entire area. The photoresist in this application is chosen, imagewise exposed and developed so that after development resist remains only in the image pattern of the desired durable mask. The durable mask material is then removed in the non-image areas by chemical washing or selective etching (etching only in those areas not covered by resist). The remaining photoresist material is then removed leaving the durable mask in a precise mask image pattern. In some applications it may be desirable to repeat the process to form multiple layers of mask having differing compositions and/or image patterns.

The structure of a preferred embodiment of this invention is illustrated in more detail in the FIG. 2 cross sectional view in which mask 12 is shown covering: (a) filter edge surface 22*a*; (b) the area of junction between the filter and the fiber 11 end face 22*b*; (c) the area of junction between the filter edge surface and the filter face 22c; and (d) the peripheral portion of the filter face surface 13 distal to the fiber 22d. The diameter of core 21a is exaggerated in this view. Correspondingly the cladding 21b is shown as much thinner than it normally would be. The approximate ratio of cladding thickness to core diameter in a monomodal fiber is generally about 20 to 1. Thus for a 120 micron fiber the core diameter would likely not exceed 6 microns. The overlap 14 of mask 12 over distal filter face periphery is also exaggerated. This overlap 14 of mask 12 is depicted in FIG. 2 as being sufficiently extensive to mask light that would otherwise impinge directly on fiber core 21a. Overlap 14 could also be a minimal overlap to extend just a short distance toward the core center covering only the peripheral portions of filter face 13 and masking only light that would otherwise impinge on cladding 21b. In a preferred embodiment overlap 14 of mask 12 on filter face 13 is circumferentially uniform, defining a circular aperture to filter face 13. In another preferred embodiment the aperture diameter is larger than the diameter of the fiber core and exposes the entire core face. Cavity 16 formed at its circumference by the overlap of mask 12 and at its side proximate the fiber by filter face 13 can be used as a nesting cavity, e.g., for a sensor or an additional filters or durable masks.

By using, for example, precision tooling, photoresist technology and/or stereo lithographic methods, the resultant masks can be of unique, complex or simple, repeatable shapes. The masks can be formed to perfectly conform to the substrate shape. The masks can also be formed to precise exterior dimensions. The mask can be formed on the fiber or can be formed on mandrel for later application to the fiber. The filter can be formed on the fiber before application of the mask, or the filter can be applied with the mask. The thickness of the mask can be extremely thin and precise for some applications where, for example, only photons of a selected wavelength are intended to pass through the mask. The thickness can be variable, for example, when an exterior mask dimension, e.g. circumference, needs to be made to a predetermined dimensional tolerance. Another example of where the thickness is desirably variable is when there is more than one layer in some areas of the mask, as described above.

Figure 3:
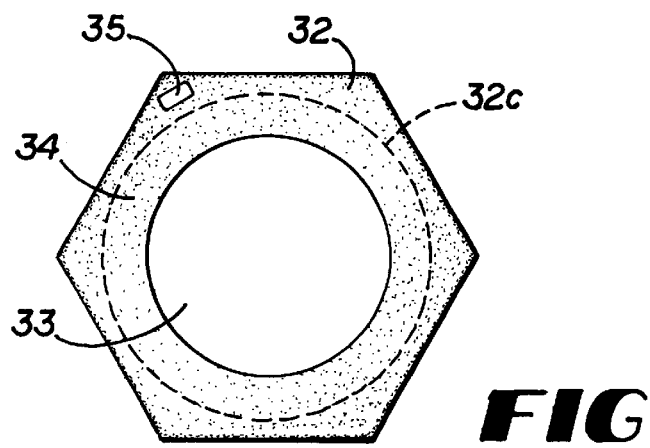
FIG. 3 is an end view of an optical assembly illustrating a mask having a hexagonal exterior profile and a circular aperture.

FIG. 3 is an end view of an optical assembly in which mask 32 has a cross sectional configuration of a hexagon for at least some of its axial length. Its aperture is circular exposing filter end face 33. The dashed circle 32c illustrates the circumference of filter end face 33 and the extent of overlap 34 of mask 32 overlapping filter end face 33. The hexagonal structure is one of a wide variety of shapes that can be chosen to accommodate coupling to other structures in a more easily fixed relationship. The identifier is conveniently located in a corner of the hexagonal mask 32 where it can have additional space and remain uncovered during manufacturing operations.

Figure 4:
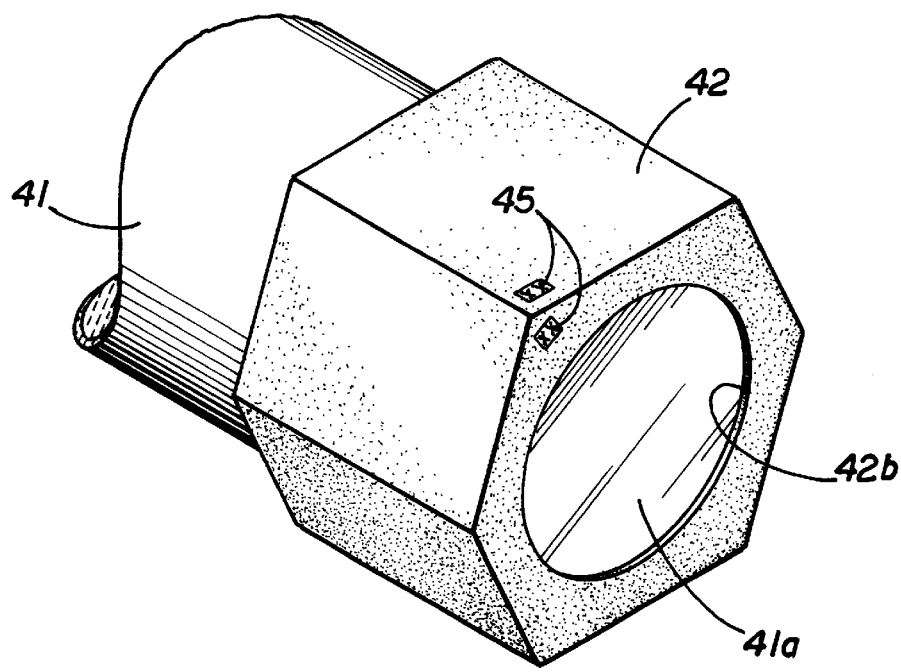
FIG. 4 is a distorted perspective of an uncompleted optical assembly end portion illustrating a mask precursor having a hexagonal profile.

In some applications, for example where space is limited, it is desirable to form the mask as a single unit in the late stage of manufacturing the assembly. However, in some larger scale production operations, for example, the mask is desirably formed in two stages. In the first stage as illustrated in FIG. 4 a mask portion 42 having a cylindrical inside surface 42b mated to or formed around, for example, optical fiber end portion 41 exposing fiber end face 41a. The outside surface 42 can be of the wide variety of shapes mentioned above for accommodating fiber coupling, with FIG. 4 illustrating a hexagonal axial external structure. Note that in this preferred embodiment identifier spaces occur on both the exterior surface 42 and the face surface of the first stage mask portion. The filter is then applied at a later stage of manufacture. The mask is also completed by adding a second stage (and any necessary additional stages) after the filter is applied to the fiber end portion 41a.

Figure 5:
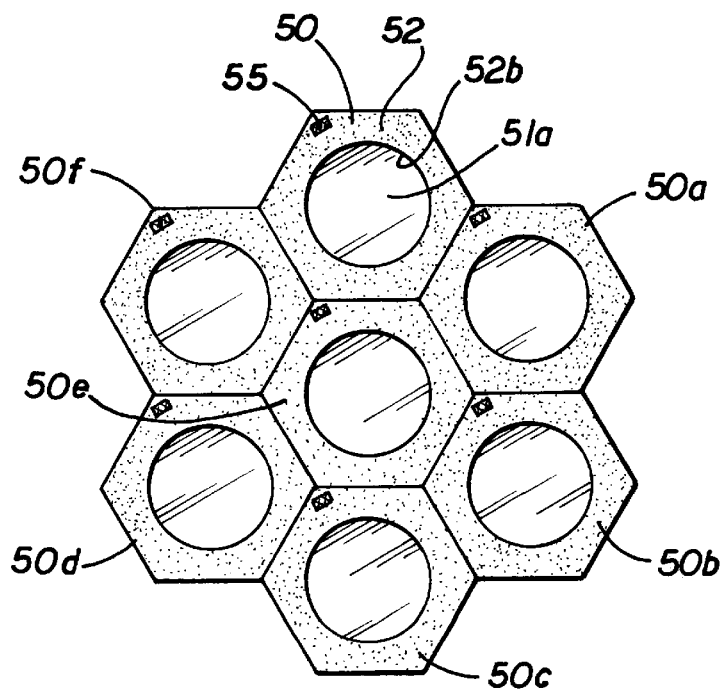
FIG. 5 is an end view of a cluster of uncompleted optical assemblies end portions.

FIG. 5 illustrates a further step in the manufacturing process in which a cluster of units of the type illustrated in FIG. 4 is accumulated. Each unit includes a mask portion (with radial thickness exaggerated) surrounding a fiber. The individual units are in compact relationship to each other. The close relationship, effectively allowing no gaps between mask portions, gives rise to significant manufacturing advantages.

One step necessary in applying high performance filters to fiber end faces is to thoroughly clean and polish the fiber end faces. Applicants have found a very effective way of accomplishing that polishing. The method is disclosed in Applicants' co-pending U.S. patent application Ser. No. 08/819, 979, filed Mar. 13, 1997, now issued as U.S. Pat. No. 5,953,477, mentioned above, which is incorporated herein by reference. In brief the method involves aggregating a large number of fiber segments in bundles with segments parallel and in intimate relationship with the end of each segment that is to be coated approximately even so that the aggregate ends form a roughly planar surface. The segments are firmly held together and polished as a single unit to a 0.3 micron finish. By holding the segments tightly together the amount of polishing debris that can get between the segments is held to a minimum. After drying the bundle multilayer filter coating is applied to the polished surface of the aggregated fibers.

Applicants have found that even after thorough washing, small particles of debris remain on some fibers. That debris can reduce the yield of acceptable filtered fibers especially with the high quality demands of today. The debris largely gets trapped in the small spaces between the generally circular fibers. One way to assure that the segments are clean is to separate the bundle and wash the fibers individually. On a small scale that is practical. However, on a large scale separating the fibers to wash them and then bundling them again for coating is difficult and cost prohibitive. Although the FIG. 5 illustration uses only seven fiber/mask units each having fiber end portion 51a encased in mask portion 52 with identifier space 55, the number of such units in a single cluster in the manufacturing process can reach into the thousands in higher volume operations.

For reasons which will become evident below each of the units in this preferred embodiment has an additional identifier space on its exterior face as illustrated in FIG. 4. Using the mask portions in the FIG. 5 illustration eliminates spaces between units. By using a bundling material that holds the mask portions compactly together and surrounds the bundle intimately, there is literally no space for debris to accumulate. In this preferred embodiment one or more locator means (e.g., bar code information) would also be fixed to or on the bundling material for holding the units together. The bundling material, for example Teflon tubing (Teflon is a DuPont trade name for a polyfluorinated hydrocarbon material) is then heat shrunk to hold the mask portions together tightly. The fiber end of the bundle is first scanned for digitization to, for example, record details from the identifier spaces as well as getting configurations of each of the fibers and their associated masks. (Fibers do not all have identical faces.) The fiber ends with mask material is polished to a 0.3 micron finish, the surface washed thoroughly and dried. The surface is again scanned thereby registering changes, for example, to fiber face dimensions. This second scanning is frequently useful but is particularly appropriate when beveled end faces are created in the polishing operation. (See FIG. 8 and U.S. application Ser. No. 08/819,979, filed Mar. 13, 1997, now issued as U.S. Pat. No. 5,953,477, mentioned above.) Depending on the assembly requirements the filter is then applied directly to the entire surface (mask material and fiber). The peripheral extremity of the filter on each unit is then removed by, for example, using photoresist and selective etching. A surface mask portion (the second stage mask portion) can then be applied also using, for example, the photoresist methods described above.

The second stage durable mask in one preferred embodiment covers all of the filter edges and any selected portions of the filter face. Additional mask layers can be added subsequently as desired with different or identical patterns. In a preferred embodiment of this invention the surface is first scanned, digitized and information about the individual fibers is recorded as indicated above. The filter is then deposited on the entire surface in the manner consistent with that set forth in applicants' copending U.S. patent application Ser. No. 09/267,258, filed Mar. 13, 1999 identified above and incorporated herein by reference. Then a first photoresist is applied, imagewise exposed, and developed to expose those areas where filter material is to be removed (for example, the remaining resist covers entire fiber surface 51a of unit 50 and areas corresponding thereto on each of the mask material-fiber units 50a–f). The filter material is then etched off as indicated above. The surface is again thoroughly cleaned. A surface mask portion is then applied. The remaining photoresist material is then removed leaving a surface of durable mask material and filter covering the fiber surface. Additional layers and/or patterns of durable mask material is applied depending on the specific intended use of the optical assembly.

FIG. 6 illustrates optical assembly 60 and 60a with the end of mask 62 of assembly 60 near the end of mask 62a of assembly 60a ready for end to end connection. A further advantage of applicants robust mask is that it can be used in end to end connections for waveguides. In FIG. 6 metallic mask 62 is aligned with 62a such that the aperture to filter 63 defined by overlap 64 mates with the corresponding aperture defined overlap 64a (hidden from view by perspective). It is important in many applications to align fiber 61 with fiber 61a to achieve maximum effectiveness. This alignment can be accomplished by using test equipment which sends light through the fibers. One fiber is rotated to achieve the correct result. Using information provided on identifier spaces 65 and 65a (in combination to reference sources that may be stated therein) the alignment is accomplished without such on site testing. Optional control port 66 is discussed with reference to FIG. 7 below.

FIG. 7 illustrates assembly 60's mask 62 end to assembly 60a's mask 62a end relationship. After aligning fibers 61 and 61a mask 62 and 62a the two are welded together by applying an electric field to the juncture seam 67. When connecting optical fibers end to end it is not uncommon for the weld to be a point of weakness for the fiber, especially when a filter is incorporated at the weld. By using applicants mask overlap as for the weld the juncture can be very strong, limited only by the specific amounts and materials used. That joint can also provide a point for connecting other components using for example, metal solders, or for controlling the electric or magnetic field inside the cavity formed by the mask overlap. That cavity can be constructively used, for example, by encapsulating a material that enhances optical performance or a wafer that may function as an amplifier, a sensor or some other useful device. Using the masks of this invention to connect fibers also decreases unwanted cross talk between fibers while making available sites for wanted communication between fibers. Optional control port 66 allows for inserting, for example, materials for filling the cavity as described above or a control light or tap into the cavity.

FIG. 8 illustrates two optical assemblies 80 and 80a having mating beveled end faces in mating orientation. In this case prior to beveling the fibers would be aligned. The bevel thereafter generally defines the mating orientation. Core 81 and 81a align and claddings 81c and 81d align. When optical assemblies 80 and 80a are brought together overlap 84 of mask 82 will meet with overlap 84a of mask 82a. Fusion of overlap 84 with overlap 84a will result in a cavity formed at its peripheral edge by overlaps 84 and 48a and at its sides by filter end faces 83 and 83a with its volume defined by the sum of cavities 86 and 86a.

Figure 9:
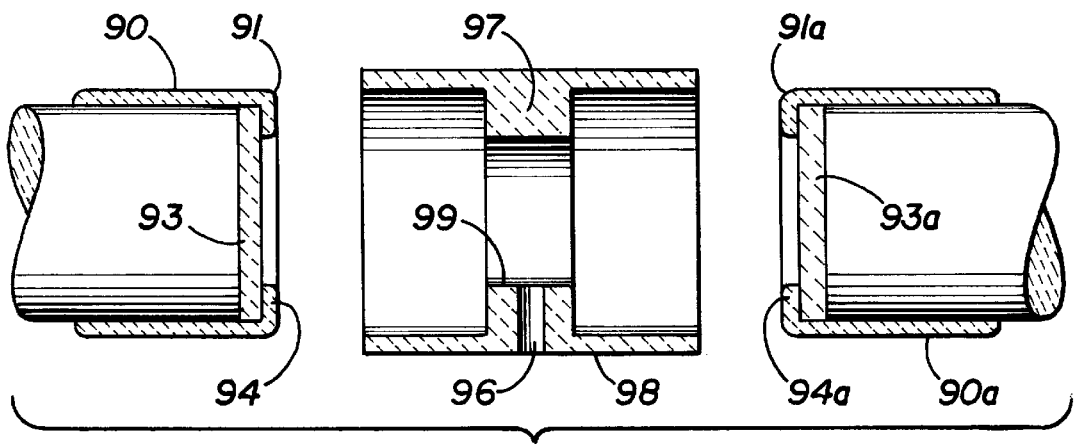
FIG. 9 is a cross sectional view illustrating two optical assemblies oriented for end to end splice using a connection device mated to the masked assembly ends.

In the FIG. 8 structure and in the structure illustrated in FIG. 6 and FIG. 7 the cavity optical length dimension is controlled by the thickness of the combined mask overlap thickness. This provides between the two filters (if each assembly has a filter) a resonant cavity of short, precise dimension. Various materials, for example, non-linear materials, polarizing structures, or light sensitive crystals, can be placed between the filters to optimize the cavity for particular purposes. Calcite provides a material base for one such polarizing structure; another polarizing material is commercially available from Corning Incorporated marketed under the trade name Polarcor. The polarizing function reduces a filter's spectral deviation to angle of incidence variation. FIG. 9 illustrates yet another advantage of the masks of this invention. To the extent one desires an optical path length longer than would be provided conveniently in the FIG. 7 and FIG. 8 illustrations, in FIG. 9 the masks 91 and 91a of optical assemblies 90 and 90a respectively in another preferred embodiment of this invention are tailored to fit conveniently into cylindrical connector 98. Overlap 94 and overlap 94a are inserted into connector 98 to butt with spacer 97 of connector 98. The length of spacer cylinder 97 is chosen so that the sum of the length of spacer cylinder 97 plus the cavity length resulting from overlap 94 and 94a (the resulting distance from filter 93 to filter 93a) is the desired resonant cavity length. Optional port 96 provides the opportunity for loading the resonant cavity with material or useful components as described with reference to FIG. 7 above. Assemblies 90 and 90a are secured to connector using, for example suitable adhesives or locking methods such as those mentioned below.

Figure 10:
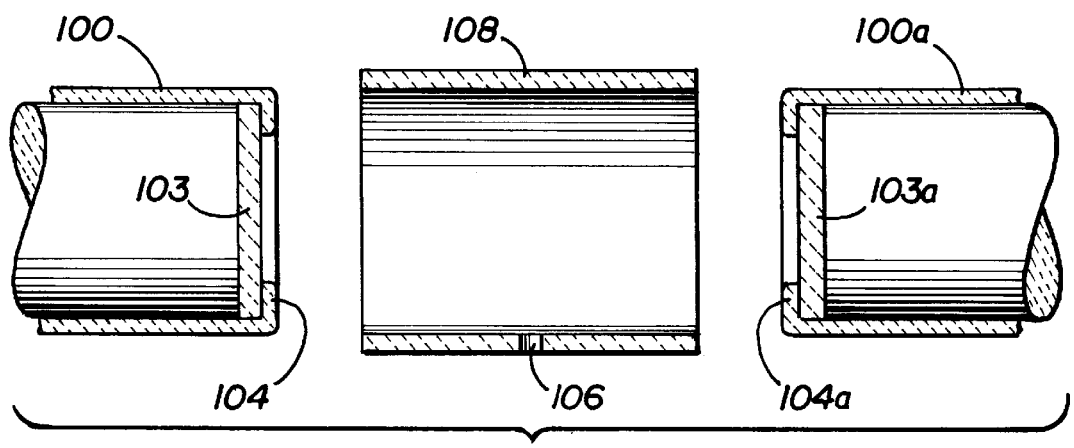
FIG. 10 is a cross sectional view illustrating two optical assemblies oriented for end to end splice using a connection device having a fluid entry/evacuation port.
Figure 11A:
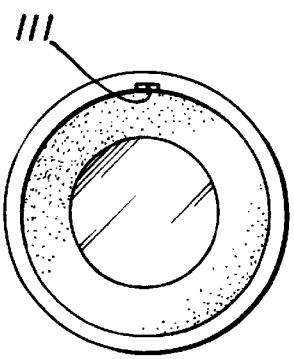
FIG. 11 includes 11a which is an end view of a splice connection device as in FIG. 10 and including a channel for aligning the fiber end faces, and 11b which is a blow-up of the channel and its surrounds.
Figure 11B:
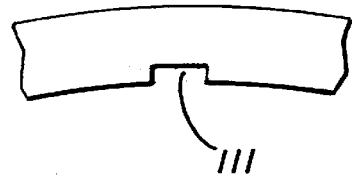

A further advantage of applicants' mask is the ease with which the masks lend themselves to standardization. Thus the mask exterior dimensions are standardized to mate with the interior of a standardized connector configuration. FIG. 10 illustrates another example of such a standard connector 108. Optical assemblies 100 and 100a are inserted into connector 108 to the point where overlap 104 meets 104a at the region where port 106 extends through the wall of connector 108. This illustrates a further use of port 106 as an evacuation port to assure intimate contact of overlaps 104 and 104a. Of course the port could also be used as described above. FIG. 11 illustrates a further enhancement of the connector showing in FIG. 11a an end view of connector 108 of FIG. 10. Connector 108 has been modified in the FIG. 11 illustration to include an alignment channel 111. Channel 111 is illustrated in more detail in blow up in FIG. 11b. The channel also provides a locking mechanism by including a turn in the channel. Masks 100 and 100a also are modified to adapt to the FIG. 11 connector by including a nub on the periphery of each of mask 100 and 100a sized to mate with channel 111. The length of the nub is sized to accommodate the channel direction turn in the locking mechanism.

As illustrated above the masks of this invention provide a convenient and effective system for manufacturing optical assemblies for high performance. The system includes a first unit with an optical fiber end connected to a high performance filter. The filter/fiber end is circumscribed by a mask that adheres to the fiber and has external dimensions and configuration that are readily reproducible. The mask preferably has a surface that protrudes onto the face of the filter, thus keeping unwanted photons from passing through edge and surface juncture areas and creating noise to an ultimate signal. The external dimensions of the mask mate with an appropriately configured female connection means. The connection means can be double ended for further connection to another fiber with a mask like that on the first unit. The connection means could also be configured to connect to another device such as a spectrophotometer. By providing a mask on the high performance filter end that has standard external dimensions and a connecting means matable with the mask the ultimate assembly of final product in high volume/high speed operations is simplified.

The present invention has been described in relation to particular embodiments that are intended in all respects to illustrate and not restrict. Other embodiments will become apparent to those skilled in the art to which the invention pertains without departing from the invention's spirit and scope. Accordingly, the scope of this invention is defined by the appended claims rather than the above description.

We claim:

1. An optical assembly comprising
   a waveguide member having at least two ends,
   a filter in optical communication with said waveguide member, said filter having a face surface facing toward one end of said waveguide member, a second face surface facing away from one end of said waveguide member, and at least one peripheral edge surface, and
   a mask adhering to at least one of said filter surfaces, said mask substantially opaque in at least one selected spectral region and impacting the extent to which photons in said selected spectral region can pass through said filter.

2. The optical assembly of claim 1, wherein said mask comprises a thin-film.

3. The optical assembly of claim 2 wherein said filter adheres to a substrate having an edge surface.

4. The optical assembly of claim 3 wherein said mask also covers a portion of said substrate edge surface of said filter.

5. The optical assembly of claim 4 wherein said waveguide member is an optical fiber.

6. The optical assembly of claim 5 wherein said mask adheres to one of said peripheral edge surfaces of said filter.

7. The optical assembly of claim 6 wherein said mask covers substantially the entire peripheral edge surface of said filter.

8. The optical assembly of claim 6 wherein said mask covers substantially the entire peripheral edge surface of said filter and also covers a portion of said second face surface of said filter.

9. The optical assembly of claim 4 wherein said filter adheres to said one end of said waveguide member.

10. The optical assembly of claim 2 wherein said mask adheres to one of said peripheral edge surfaces of said filter.

11. The optical assembly of claim 10 wherein said mask covers substantially the entire peripheral edge surface of said filter.

12. The optical assembly of claim 11 wherein said mask also covers a portion of said second face surface of said filter.

13. The optical assembly of claim 2 wherein said thin film is metallic.

14. The optical assembly of claim 13 wherein said filter comprises thin-film layers of alternating refractive index.

15. The optical assembly of claim 2 wherein said mask adheres to a portion of one of said face surfaces of said filter.

16. The optical assembly of claim 15 wherein said mask adheres to a portion of the second face surface of said filter.

17. The optical assembly of claim 1 wherein said mask covers the portion of said second face surface adjacent a junction between said second face surface and one of said peripheral edge surfaces, and said mask further covers at least the portion of said peripheral edge surface adjacent said junction.

18. The optical assembly of claim 17 wherein said mask comprises a thin-film layer.

19. The optical assembly of claim 18 wherein said mask covers substantially one of said peripheral edge surfaces of said filter and covers the periphery of the edge of said fiber positioned adjacent to said filter.

20. The optical assembly of claim, 18 wherein said mask comprises a thin-film metallic layer.

21. The optical assembly of claim 17 wherein said filter comprises thin-film layers of alternating refractive index.

22. The optical assembly of claim 17 wherein said first waveguide member is an optical fiber and said filter is in intimate contact with said fiber.

23. The optical assembly of claim 1 wherein said filter comprises thin-film layers of alternating refractive index.

24. The optical assembly of claim 1 wherein said filter comprises a dielectric stack with a packing density of at least 95%.

25. The optical assembly of claim 24 wherein said mask is substantially transparent to light in a first spectral region and at least substantially opaque to light in a second spectral region.

26. The optical assembly of claim 1 wherein said filter comprises a multi-layer high performance thin-film filter with a packing density of at least 95%.

27. The optical assembly of claim 1 wherein said waveguide member is monomodal.

28. The optical assembly of claim 1 wherein said waveguide member tapers down away from said filter.

29. The optical assembly of claim 1 wherein said waveguide member is a monomode waveguide and includes an up taper towards said filter and said filter comprises a dielectric stack with packing density of at least 95%.

30. An optical assembly comprising
    a waveguide having at least one end face,
    a thin-film filter in optical communication with said waveguide, said filter having a first face surface optically closer to said waveguide end face and a second face surface opposed to said first face, and
    a mask in intimate contact with at least one of said filter surfaces, said mask substantially opaque in at least some spectral region.

31. The optical assembly of claim 30 wherein said waveguide is an optical fiber having at least one end face, and said filter comprises said first face surface facing toward and said second face surface facing way from one end of said fiber.

32. The optical assembly of claim 31 wherein said mask is in intimate contact with the second face surface and defines a pattern by which photons can pass through said second face surface.

33. The optical assembly of claim 32 wherein said mask covers at least the portion of said second face surface adjacent a junction between said second face surface and a peripheral edge surface of said filter, said mask further covering at least a portion of said peripheral edge surface adjacent said junction.

34. The optical assembly of claim 33 wherein said mask covers substantially said peripheral edge surface of said filter.

35. The optical assembly of claim 34, wherein said filter first face is in intimate contact with said one end face of said optical fiber.

36. The optical assembly of claim 35 wherein said mask also covers a portion of walls of said fiber.

37. The optical assembly of claim 36 further comprising a second fiber having an end joined to the second face surface of the filter.

38. The optical assembly of claim, 37 wherein the second fiber comprises a fiber wall and a face, and wherein at least a portion of the fiber wall is positioned adjacent the face of the second fiber and is covered by the mask.

39. The optical assembly of claim 38 wherein the mask of each of the first and second fibers is shaped for-mating to each other.

40. The optical assembly of claim 39 wherein each of said masks is a part of a mask matching and connecting assembly for precision fiber-to-fiber connection.

41. The optical assembly of claim 38 wherein said mask extends to cover at least a portion of the second fiber face.

42. The optical assembly of claim 37 wherein the second fiber comprises a face and at least a portion of the second fiber face is covered by the mask.

43. The optical assembly of claim 37 wherein said second fiber end is covered by a filter.

44. The optical assembly of claim 35 wherein at least said first filter face is specially shaped for mating with said one end face of said fiber.

45. The optical assembly of claim 31 wherein said mask comprises a thin film.

46. The optical assembly of claim 45 wherein said thin film comprises metal.

47. The optical assembly of claim 31 wherein said mask is rigid.

48. The optical assembly of claim 30 wherein said waveguide is monomodal.

49. The optical assembly of claim 30 wherein said waveguide tapers down away from said filter.

50. The optical assembly of claim 30 wherein said waveguide is a monomode waveguide having an up taper towards said filter wherein said thin film is comprised of material having packing density exceeding 99%.

51. The optical assembly of claim 30, said filter further comprising a peripheral edge surface, said mask positioned in intimate contact with said peripheral edge surface.

* * * * *